(12) United States Patent
Bell et al.

(10) Patent No.: US 6,610,542 B1
(45) Date of Patent: Aug. 26, 2003

(54) EFFICIENT EX VIVO EXPANSION OF CD4+ AND CD8– T-CELLS FROM HIV INFECTED SUBJECTS

(75) Inventors: David N. Bell, Oakville (CA); Kenneth Lee Rosenthal, Ancaster (CA)

(73) Assignee: Hemosol Inc., Etobicoke (CA)

( * ) Notice: Subject to any disclaimer, the term of this patent is extended or adjusted under 35 U.S.C. 154(b) by 0 days.

(21) Appl. No.: 09/296,402

(22) Filed: Apr. 23, 1999

Related U.S. Application Data

(60) Provisional application No. 60/082,861, filed on Apr. 24, 1998.

(51) Int. Cl.$^7$ .................. C12N 5/00; C12N 15/00; A01N 63/00; A61K 31/70; C07K 1/00
(52) U.S. Cl. ............ 435/377; 435/320.1; 435/325; 435/455; 424/93.21; 424/93.2; 514/44; 530/350; 530/351
(58) Field of Search .................. 514/44; 435/325, 435/377, 320.1, 69.1, 455; 424/93.71, 130.1, 143.1, 93.21, 93.2; 530/350, 351

(56) References Cited

U.S. PATENT DOCUMENTS 6,194,207 B1 * 2/2001 Bell et al. .................. 435/377

FOREIGN PATENT DOCUMENTS

WO WO9808537 3/1998

OTHER PUBLICATIONS

Bazan et al., Patterns of CCR5, CXCR4, and CCR3 usage by envelope glycoproteins from human immunodeficiency virus type 1 primary isolates, 1998, Journal of Virology, vol. 72, pp. 4485–4491.*

Riley et al., Naive and memory CD4 T cells differ in their susceptibilities to human immunodeficiency virus type 1 infection following CD28 costimulation: implications for transmission and pathogenesis, 1998, Journal of Virology, vol. 72, pp. 8273–8280.*

Carrol et al., Differential regulation of HIV–1 fusion cofactor expression by DC28 costimulation of CD4+ T cells, 1997, Science, vol. 276, pp. 273–276.*

Levine et al., Antiviral effect and ex vivo CD4+ T cell proliferation in HIV–positive patients as a result of CD28 costimulation, 1996, Science, vol. 272, pp. 1939–1943.*

Rosenberg, Gene therapist, Heal thyself, 2000, Science, vol. 287, p. 1751.*

Verma, Gene therapy, 2000, Molecular Therapy, vol. 1, p. 493.*

Friedmann, Principles for human gene therapy studies, 2000, Science, vol. 287, pp. 2163–2164.*

Anderson, Human gene therapy, 1998, Nature, vol. 392, pp. 25–30.*

Verma et al., Gene therapy–promises, problems and prospects, 1997, Nature, vol. 389, pp. 239–242.*

Varmus, Gene therapy: Not ready for prime time, 1996, Nature Medicine, vol. 2, pp. 7–8.*

Levine et al. (*Science*, 272:1939, Jun. 28, 1996).
Moran Aids Research and Human Retroviruses 9:455 (1993).
Wu et al. (Genes Dev 5:2128 (1991)).
Kamine et al. (Virology 182:570 (1991)).
Kuppuswamy et al. (Nucleic Acids Research 17:3551–61, (1989)).
Kinter et al. PNAS USA 93(24): 14076 (1996).
Skea, Blood 90:3680 (1997).

* cited by examiner

*Primary Examiner*—Jeffrey Fredman
*Assistant Examiner*—Sumesh Kaushal
(74) *Attorney, Agent, or Firm*—Bereskin & Parr; Micheline Gravelle

(57) ABSTRACT

Methods for the expansion of CD4, CD8, and DP T-cells from HIV infected patients are disclosed which allow the maintenance of low levels of HIV. The invention further discloses methods for the inhibition of HIV gene expression. Also disclosed are methods for the rapid and efficient screening of cells derived from HIV-infected patients to assess the suitability of various antiviral treatments. The invention further provides a means for the generation of cell banks for use in immune reconstitution and means of treating or modifying expanded cell populations prior to infusion to enhance or modulate therapeutic effectiveness.

33 Claims, 4 Drawing Sheets

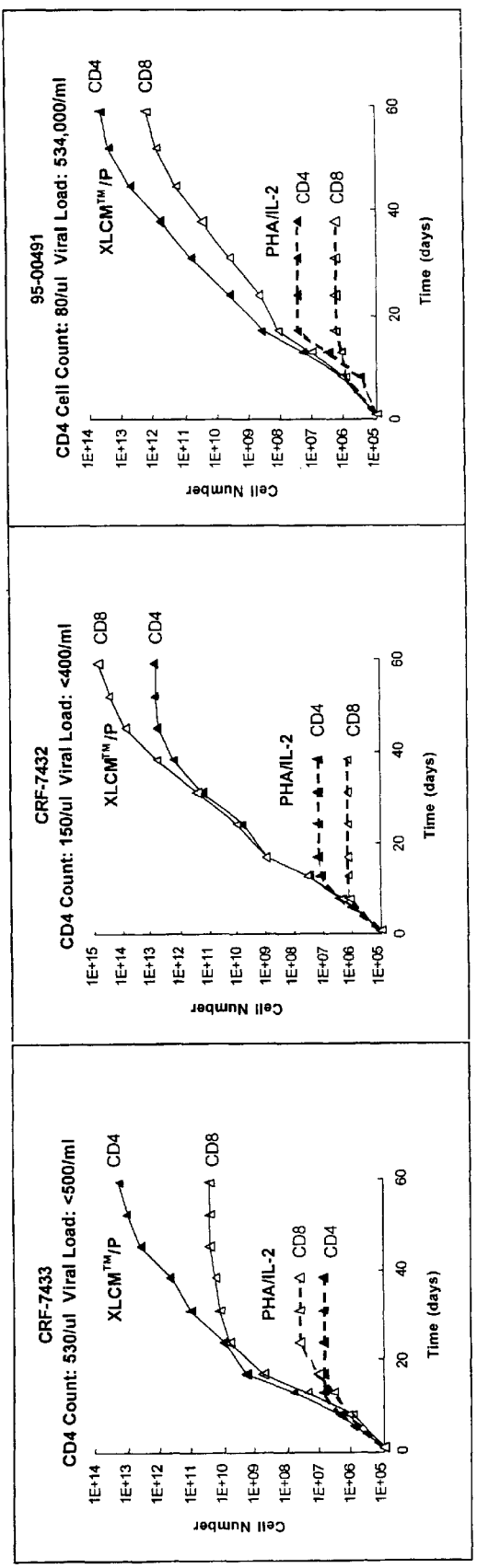
Figure 1. Expansion of Enriched CD4+ and CD8+ T Cells from HIV+ Donors by XLCM™

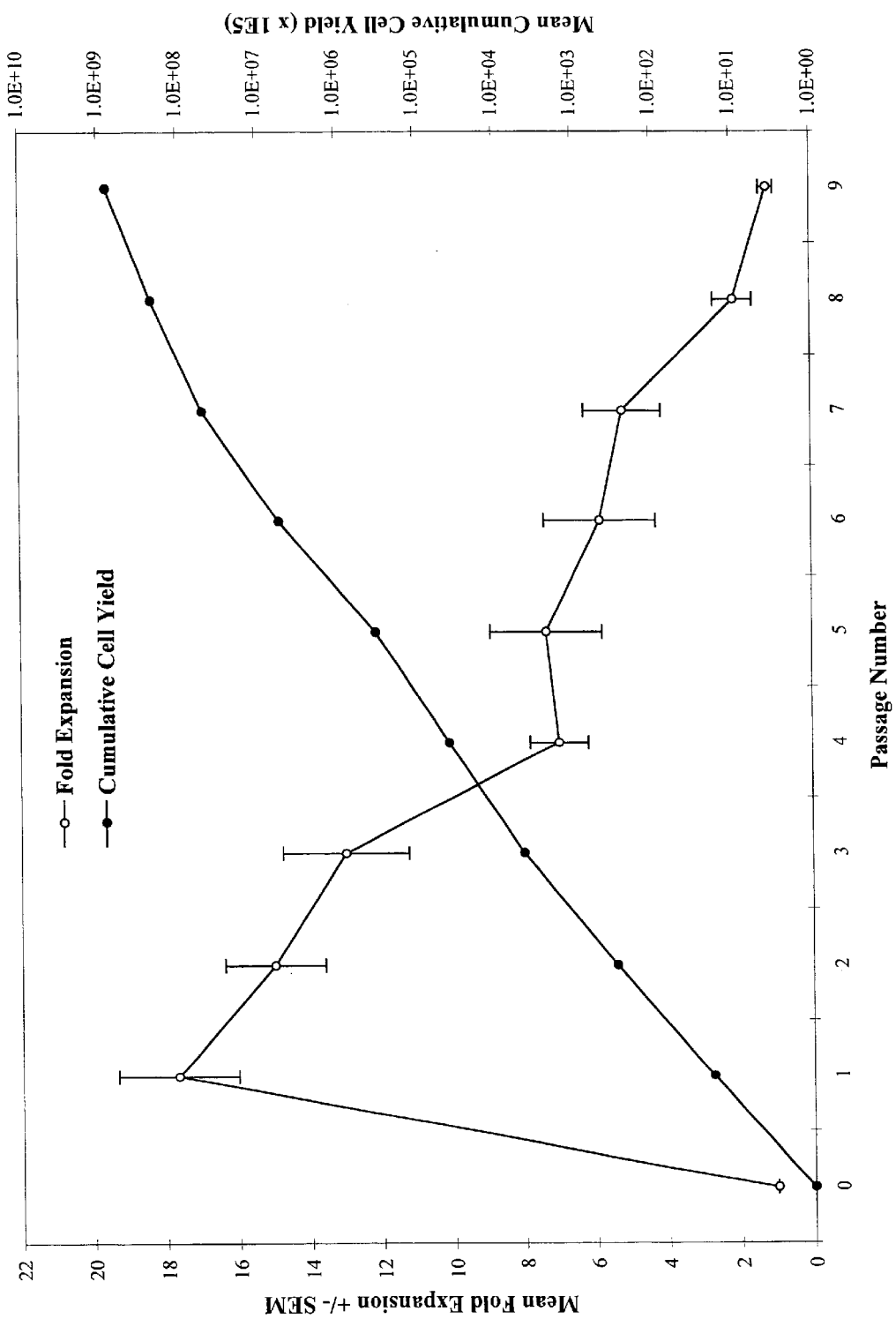

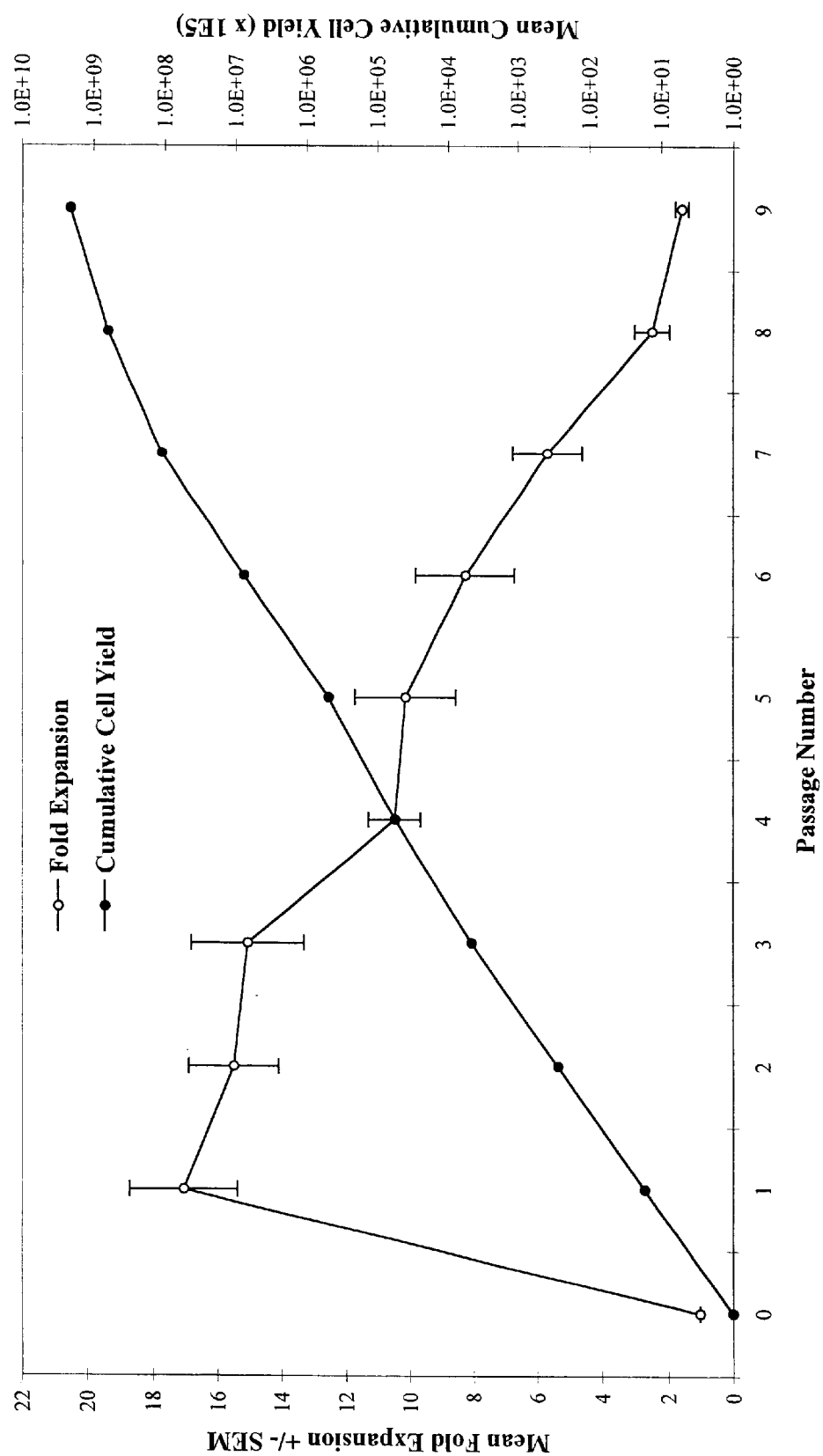
Figure 3: Expansion by CM/P of CD8+ T Cells from HIV+ Patients

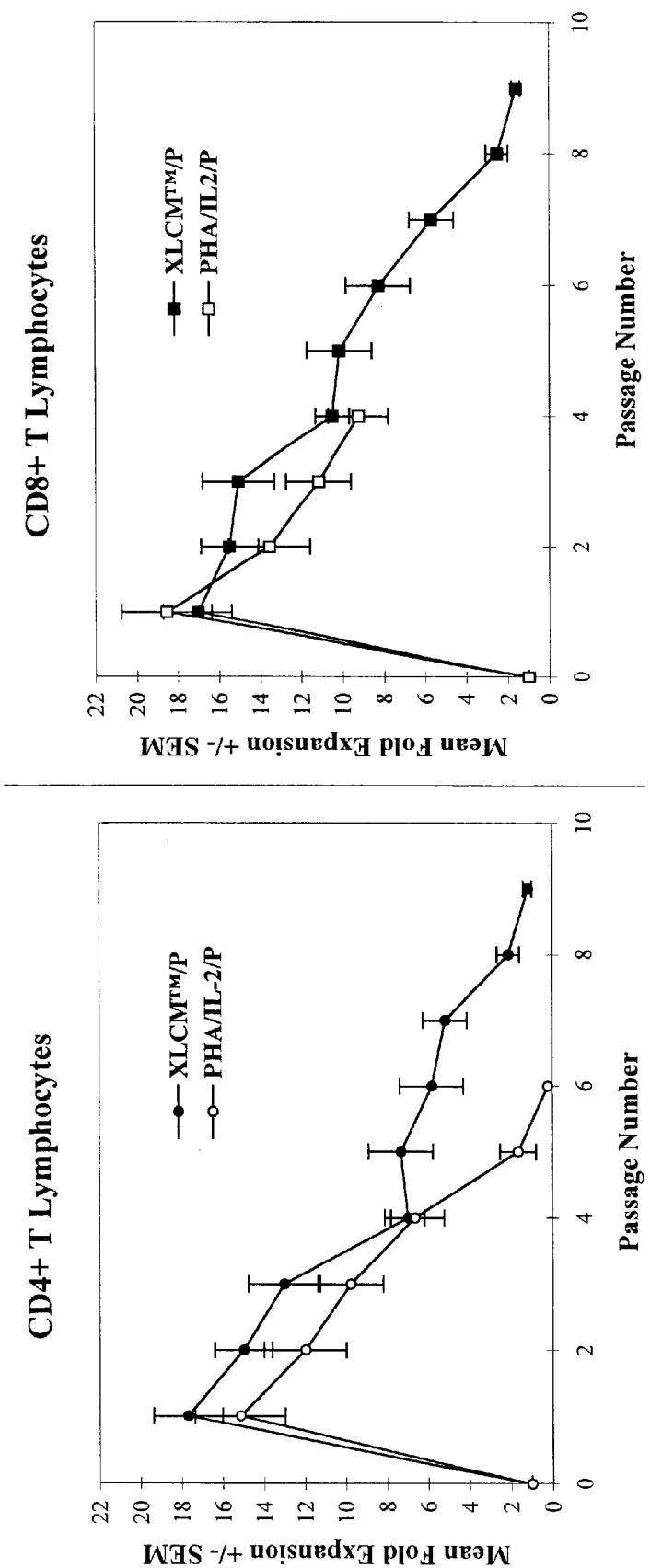
Figure 4: Expansion of T Cells from HIV+ Patients by CM/P Compared to PHA/IL-2/P

EFFICIENT EX VIVO EXPANSION OF CD4+ AND CD8- T-CELLS FROM HIV INFECTED SUBJECTS

This application claims priority to a U.S. Provisional Application Ser. No. 60/082,861, filed Apr. 24th, 1998.

BACKGROUND OF THE INVENTION

The human immunodeficiency virus (HIV) is a serious and growing health threat in virtually every part of the world. It has been estimated that over 22 million people are currently infected worldwide, and it is anticipated that over 40 million people will be infected by the end of this decade.

HIV infection typically leads to acquired immunodeficiency syndrome (AIDS) within 8 to 10 years after infection. Individuals with AIDS are subject to opportunistic infections and cancers, leading to severe illness and, ultimately, death. Although various treatments delaying the progression from HIV infection to AIDS are known, these treatments are of limited effectiveness and generally require the use of pharmaceuticals which have adverse side-effects. Moreover, the effectiveness of different drug treatments varies among individuals and no satisfactory system exists to screen different drug combinations for effectiveness in combating HIV infection in a particular subject.

HIV is a retrovirus, closely related to simian immunodeficiency virus (SIV). At least three variants of HIV, known as HIV-1, HIV-2, and HIV-0, are known. It is believed that HIV-1 is the predominant global form of human HIV infection at the present time. HIV-2 is believed to be common in West Africa, but rarer elsewhere in the world. HIV-2 appears to be less pathogenic that HIV-1. In addition to these three HIV variants, the high natural mutation rate of HIV DNA means that virtually every individual infected with HIV carries a slightly different virus. Differences between HIV isolates complicate efforts to devise effective anti-HIV approaches, including drugs and vaccines.

HIV enters target cells by the binding of gp120 (present on the HIV virion) to cellular receptors, followed by fusion of the viral envelope with the plasma membrane of the target cell. The major cellular receptor for the HIV gp120 is cluster of differentiation factor 4 (CD4). The highest levels of CD4 are generally found on T-helper (Th) cells; thus, the consequences of HIV infection are typically most obvious in the Th cell population. HIV can also infect other cells, including macrophages, monocytes, dendritic cells, Langerhans cells, and microglial cells. HIV-1 has a higher affinity for CD4 than does HIV-2, and it is thought that this may contribute to the greater pathogenicity of HIV-1 compared to HIV-2. HIV-1 also requires a chemokine coreceptor (e.g. CCR5 or CXCR4) to gain entry into susceptible cells.

There is evidence in the prior art suggesting that specific chemokines such as RANTES, MIP-1α and MIP-1β may inhibit fusion between the HIV-1 virion and target cells by inhibiting the interaction between HIV surface proteins and cell surface receptors. This inhibits viral replication by reducing the rate of infection.

Fusion between the HIV virion and the plasma membrane of the target cell allows the HIV RNA to enter the target cell, where it is reverse transcribed into DNA by viral reverse transcriptase and integrated into the host cell's genome to form an HIV provirus. Once the HIV DNA is integrated into the host cell genome, it is replicated during cell division and is passed on to daughter cells.

The HIV provirus may remain inactive in the host cell for some time until it is activated. Upon activation, HIV structural genes are expressed, and single stranded HIV RNA (HIV ssRNA) is transcribed. The HIV structural proteins and HIV ssRNA assemble to form numerous virus particles which then exits from the host cell infects other cells.

At present, methods of inhibiting HIV replication in tissue samples have tended to focus on reducing the number of newly infected cells through the inhibition of infection by released virus particles. This has been effected through the use of compounds which inhibit fusion between the HIV virion and the plasma membrane, and inhibitors of viral reverse transcriptase (necessary to generate DNA from the viral RNA prior to integration into the host cell genome) to form the provirus. In addition, the production and release of viral particles from infected cells has been inhibited through the use of protease inhibitors which interfere with the post-translational processing of HIV gene products necessary for virus particle formation. The effectiveness of many current therapies is limited by the capacity of the HIV virus to mutate, resulting in the development of resistance. Methods for inhibiting the expression of HIV DNA in populations comprising CD8 and CD4 cells from infected subjects (thereby reducing the number of virus particles which can be formed) while greatly expanding CD4 and CD8 cells in these populations are not known in the art. Such methods might be less susceptible to circumvention by acquired resistance and therefore represent a potentially powerful form of HIV treatment.

It is desirable to have a means of inhibiting the expression of HIV DNA in infected cells. Individual infected cells are capable of producing a massive number of infectious HIV particles, and the release of such particles from a cell can cause the infection of numerous previously uninfected cells Levine et al. (*Science*, 272:1939, Jun. 18, 1996) have reported that the interaction of CD4 cells with immobilized (but not soluble) CD28 monoclonal antibodies reduces the susceptibility of CD4 cells to HIV infection. However, it would be more efficient to inhibit the formation of HIV particles in infected cells, rather than to simply attempt to reduce the rate of infection by such particles following their formation and release from the infected cell.

HIV DNA sequences are flanked by long terminal repeats (LTRs). Promoter and enhancer sequences are located in the 5' LTR, and polyadenylation sequences are contained in the 3' LTR. The 5' LTR sequence normally has only a low affinity for RNA polymerase, causing premature truncation of transcription products and preventing the formation of infectious viral particles. However, the viral protein Tat is capable of interacting specifically with a region (TAR) on the emerging RNA transcript and increasing the formation of full-length proviral transcripts.

One of the characteristic features of HIV infection is a reduction in the number of CD4+ T-cells ("CD4 cells") in the peripheral blood of infected subjects. Healthy uninfected individuals typically have approximately 1100 CD4 cells per microliter of whole blood. After an individual has been infected with HIV, CD4 cell levels generally drop gradually over a period of 8 to 10 years, but then drops more rapidly. In subjects with AIDS, CD4 cells levels below 200 cells per μl are common.

It is believed that in the early stages of HIV infection CD4 cells are destroyed at a high rate. However, at this stage the subject's immune system is able to replace many of the destroyed cells, resulting in only a gradual decline in observed CD4 cell numbers. Cells may be destroyed by various means following infection. One means for the destruction of infected cells is lysis resulting from the exit of large numbers of newly formed virs particles. A second means by which infected cells may be destroyed is by an immune response to HIV antigens expressed on the cell membrane. It is believed that enhanced levels of active anti-HIV specific CD4 cells in HIV infected patients allows the maintenance of low viral loads and non-progression into AIDS.

It appears that many uninfected CD4 cells lose their capacity to respond to foreign antigens and are also destroyed during HIV infection. The exact mechanism by which this occurs is not fully understood. However, it is suspected that free gp120 to CD4 molecules on the surface of uninfected cells. This binding may lead to the internalization of the gp120 by the uninfected CD4 cells. Proteolytic processing of the internalized gp120 in the endosome, followed by association of the processed peptides with class II MHC, may lead to the expression of an HIV peptide-MHC complex at the surface of uninfected cells. Such cells may thus be destroyed as a result of an immune response directed at the peptide-MHC complex. Additionally, the binding of free gp120 to CD4 molecules on uninfected cells may interfere with the ability of these CD4 molecules to interact with class II MHC molecules on antigen-presenting cells, thereby reducing the ability of the uninfected cell to participate in an immune response to foreign antigen. Alternately, the binding of gp120 to CD4 molecules on an uninfected CD4 cell may stimulate the production of an inappropriate activation signal, which may lead to apoptosis. It has also been postulated the free gp120 may bind to CD4 molecules on developing thymocytes, interfering with normal T cell maturation processes. Additionally, there is evidence suggesting that a single CD4 cell infected with HIV can fuse with large numbers of uninfected CD4 cells, forming a syncytium. Syncytia appear capable of producing large numbers of viral particles over a short period of time before they die.

There is evidence indicating that CD4 cell populations from subjects with AIDS have a significantly reduced ability to proliferate in response to specific antigens. This selective loss of responsiveness has been hypothesized to be the result of an inappropriate activating signal received by CD4cells, leading to cellular anergy or apoptosis.

A shift in cytokine production by CD4 cells has been observed during the progression toward AIDS. As the disease progresses, the production of the Th1-type cytokines IL-2 and IFN-$\gamma$ decreases and the production of the Th2 type cytokine IL-10 (and for a limited time IL-4) increases. This may reflect a shift from a Th1-type cellular immune response to a Th2-type humoral immune response. The reduction in IL-2 levels observed following HIV infection appears to impair the ability of CD8 cells to form cytotoxic T-lymnphocytes, reducing the subject's ability to eliminate virus-infected cells and tumour cells. IFN$\gamma$ has been reported to induce an anti-viral state in cells, and reduced IFN$\gamma$ levels following HIV infection may undermine this mechanism of cellular defense. Furthermore, IL-2 and IFN$\gamma$ activate natural killer cells ("NK cells") which are important in the very early stages of viral infection.

The cellular depletion observed following HIV infection appears to primarily affect the CD4 cell population. However, the infection and eventual loss of dendritic cells may play an important role in disease progression. Dendritic cells are major antigen presenting cells and are important to T cell activation. Dendritic cells are also important in the maintenance of functional lymph nodes, wherein T cell and B cell activation occurs.

It has been estimated that subjects infected with HIV, but not yet diagnosed as having AIDS, lose approximately two billion CD4 cells each day. While some of these cells will be replaced by the subject's own immune system, cell numbers eventually decline. Additionally, free gp120 may interact with uninfected CD4 cells of HIV-infected subjects, thereby reducing the effectiveness of surviving CD4 cells. It has therefore been proposed to produce large populations of CD4 cells for transfusion into HIV-infected subjects to replace cells destroyed or inactivated due to infection.

CD8 cell levels in the blood of HIV infected subjects are typically near normal. However, cytotoxic T lymphocyte ("CTL") activity is generally impaired in AIDS patients. Cell mediated immune responses are the principle immunological defense to HIV infection and a vigorous CTL response early in infection has been associated with a lower rate of disease progression. CTL's are the major effector cells in this antiviral response. However, the decline in CTL activity observed following HIV infection suggests that anti-HIV activity by CTL's is impaired. Thus, it desirable to have a means to induce the formation and/or proliferation of CTL's, and, even more preferably, the formation of HIV-specific CTL's. It would also be highly desirable to have a means of expanding CD4 cells, CD8 cells and CD4$^+$ CD8$^+$ T-cells ("DP cells") from HIV infected subjects, particularly if this could be accomplished while keeping viral levels in the cultured cells low. DP cells represent an early stage in T cell development and can mature to form CD4 cells or CD8 cells having varying antigenic specificities.

In order to maximize the effectiveness of treatment with expanded T cells, it is desirable that the infused cells be MHC compatible with the subject's tissue. Ideally, the best MHC match will be obtained by using the subject's own cells for infusion. However, it would be inadvisable to remove large numbers of cells from the blood of an HIV-infected patient for culture or expansion, as this may further compromise the subject's ability to mount effective immune responses against foreign antigens.

SUMMARY OF THE INVENTION

It is an object of the invention to provide a method to expand a population of T cells from HIV-infected subjects which will allow the production of enough cells to be effective in bolstering the subject's immune response from an initial sample which is small enough so that its removal does not pose a significant health risk to the subject.

It is a further method of the invention to provide a method of expanding a cell population contain HIV-infected cells which does not lead to the production of high levels of HIV in the expanded population.

It is a further object of the invention to provide a method to interfere with the expression of HIV DNA in the expanded cell population.

It is a further object of the invention to provide a use of CM to inhibit the expression of HIV DNA in a cell infected with an HIV provirus.

It is a further object of the invention to provide a method of screening cell populations derived from HIV infected subjects for susceptibility to one or more anti-HIV treatments.

It is a further object of the invention to provide a use for CM in screening cells from HIV infected subjects for susceptibility to one or more anti-HIV treatments.

It is a further object of the invention to provide a use for CM to generate cell banks.

It is a further object of the invention to provide a composition of matter comprising an expanded population of CD8 cells derived from an HIV infected patient.

It is a further object of the invention to provide a composition of matter comprising an expanded population of DP cells derived from an HIV infected patient.

It is a further object of the invention to provide a use of CM to obtain a late culture cell population from a T cell sample obtained from an HIV infected subject.

It is a further object of the invention to provide a composition of matter comprising a substantially pure late culture population derived from a T cell population obtained from an HIV infected subject.

BRIEF DESCRIPTION OF THE DRAWINGS

In the accompanying drawings:

FIG. 1 is a graphical depiction of the results of Example 3 examining the expansion of cell populations enriched for CD4 cells and CD8 cells obtained from three HIV infected subjects and cultured in CM/P or PHA/IL-2.

FIG. 2 is a graphical depiction of the results of Example 3 examining the expansion in CM/P of a cell population obtained from HIV infected subjects and enriched in CD4 cells.

FIG. 3 is a graphical depiction of the results of Example 3 examining the expansion in CM/P of a cell population obtained from HIV infected subjects and enriched in CD8 cells.

FIG. 4 is a graphical depiction of the results of Example 3 examining the expansion in CM/P and PHA/IL-2/of CD4 cells and CD8 cells obtained from HIV infected subjects.

DETAILED DESCRIPTION OF THE PREFERRED EMBODIMENTS

As embodied and broadly described herein, the present invention is directed to methods for the expansion of Cb4, CD8, and DP cell populations with reduced levels of HIV from cells derived from HIV infected subjects. In this application, the phrase "reduced levels of HIV" means a lower viral load or lower supernatant $p24^{gag}$ ("p24") level per viable T cell than what is observed in a sample from the same source, cultured in a similar manner, in RPMI-1640 medium supplemented with 10% heat inactivated pooled normal human serum (from non-HIV infected donors) and soluble anti-CD3 antibodies (1 µg/ml) (as described in Moran, *AIDS RESEARCH and HUMAN RETROVIRUSES* 9:455 (1993). The quantity of soluble p24 in cell culture supernatants is a common measure of HIV levels. Soluble p24 levels may be determined by standard methods. A preferred method is ELISA. The ELISA detection limit for p24 varies somewhat depending on reagents and conditions but is typically approximately 0.005 ng/ml. The viral load is another common measure of the levels of the HIV gag sequence from cell culture supernatants. The levels of HIV gag in supernatants may be determined by standard methods. A preferred method is reverse-transcriptase PCR ("RT-PCR") amplification which typically had a detection limit of about 400–500 HIV gag copies/ml.

The present invention is also directed to a method for screening populations comprising HIV infected cells obtained from a particular patient to assess the effectiveness of various antiviral treatments, including the ex vivo culture of T-cells in CM. Additionally, the present invention is directed to methods for the inhibition HIV gene exrsson.

Current methods of cell expansion cannot generate large expanded populations of both CD4 and CD8 T cells from a single initial sample obtained from an HIV positive subject. Surprisingly, it has been discovered that culture of a small initial mononuclear cell population derived from HIV infected subjects in the presence of a conditioned medium (CM) allows the large expansion of populations of CD4 cells, CD8 cells, and DP cells. This allows the production of cell banks containing T cells of different types suitable for use in immune reconstitution. Even more surprisingly, it has been discovered that following expansion in CM, the viral load in the resultant expanded population is low. In relative terms, the HIV viral load or supernatant p24 levels observed in cell populations from appropriate subjects expanded by the method of the invention are lower than the levels observed in cell populations from the same source expanded in RPMI-1640 medium containing 10% beat inactivated pooled normal human serum (from non-HIV infected donors) and 1 µg/ml soluble anti-CD3 antibody. In absolute terms, supernatant p24 levels in suitable subjects are below 1 ng/ml and in very suitable subjects they are equal to or less than 0.1 ng/ml. Extremely suitable subjects, the culture of whose cells by the method of the invention yields supernatant p24 levels below 0.005 ng/ml, are often observed. It is possible to identify appropriate patients, suitable patients, very suitable patients, and extremely suitable patients using the screening method of the invention.

The present invention also teaches a method of screening T cell populations derived from individual HIV-infected patients to determine their responsiveness to different antiviral therapies, including culture in CM, and treatment with other antiviral agents such as human plasma and drugs including reverse transcriptase inhibitors and protease inhibitors such as Zidovidine, Lamivudine, Indinavir, Zerit, Saquinavir, Nelfinavir, and Ritonavir, separately or in combination.

Conditioned Medium (CM) and Its Production

The conditioned medium CM used in the process of the present invention comprises a mixture of cell factors having a balance of stimulatory and inhibitory effects favouring the proliferation of the desired cell population. The CM composition is produced by treating a starting cell population with an inducing agent which includes at least one plant mitogen Preferred plant mitogens include plant lectins such as concanavalin A (ConA) or phytohemagglutinin (PHA), and T-cell mitogens such as mezerein (Mzn) or tetradecanoyl phorbol acetate (TPA). Especially preferred is a combination of ConA and Mzn. Other mitogens of non-plant origin, including interferons of various kinds, may be used in addition. The starting cell population used to prepare the CM may comprise peripheral blood cells, umbilical cord blood cells, bone marrow cells, mixtures of two or more types of such cells, or fractions or mixed fractions of such types of cells. The starting cell population may be induced by adding the inducing agent(s) to an appropriate suspension thereof in aqueous nutrient-containing medium. The CM inducing process may be affected by factors produced by the cells during culture, and by culturing conditions such as the medium used, temperature, time of culture, pH exogenous recombinant growth factors, nutrients, etc. The medium used may be serum free.

Blood cells used in the preparation of CM may be derived from healthy subjects or HIV infected donors and may be further enriched in mononuclear cells such as those obtained in the buffy coat fraction or by density gradient centrifugation. The T cells to be expanded ("initial population") and the starting cells used in the preparation of CM ("starting population") may be the same or different cell population. Furthermore, the cells may be derived from the same or different donors. CM may be prepared using starting cells from a patient obtained from one blood sample and the target lymphocyte population may be obtained from the same patient on the same or a second visit. Where the starting population is derived from an HIV infected subject, it is preferable to selectively remove HIV virions from the CM prior to use.

When used to expand autologous T cells, patient-derived CM has the added advantage of allowing the entire procedure to use biological components derived from only one person. The culture conditions and methods may be varied to produce a desired CM or the desired T cell proliferation. CM is typically prepared from approximately 50 ml of whole peripheral blood, over a culture period of 4 days. Target T cells are typically derived from between 10 and 50 ml of low density mononuclear cells and are expanded over a period of between 1 and 4 weeks.

Unlike conventional methods in which the significant expansion of only CD4 cells occurs, the present invention also allows the expansion of populations of CD8 and DP cells. CD8 cells may be expanded together with significant levels of CD4 cells in the same culture. Alternately, CD8 cells may be preferentially expanded in a separate culture. A preferred method for the preferential expansion of CD8 cells is the positive selection of CD8 cells from LDMNC's by conventional means prior to culture in CM. The addition of P further enhances the preferential production of CD8 cells, as does culture for 3 to 4 weeks.

T cells may be expanded from subjects having reduced T cell counts. However, as the method of the invention allows the expansion of an initial cell population, the higher the actual number of cells capable of forming target cells in the initial population, the higher the absolute number of target cells which can be produced by the method of the invention over a fixed time period. Thus, while the large rate of cell expansion provided by the method of the invention allows the production of therapeutically useful numbers of CD4 cells from subjects with CD4 cell counts as low as 50 cells/$\mu$l, higher CD4 counts are preferable. In a preferred embodiment of the invention the subject providing the initial population has >100 CD4 cells/$\mu$l. In a more preferred embodiment of the invention, the subject has >200 CD4 cells/$\mu$l, even more preferable >400 CD4 cells/$\mu$l. In a yet more preferred embodiment, the subject has >800 cells/$\mu$l. Similarly, it is preferable that the subject providing the initial population have CD8 cell counts >200 cells/$\mu$l, more preferably >400 cells/$\mu$l, and even more preferably >800 cell/$\mu$l.

In order to examine the mechanisms contributing to the low viral loads observed in cell populations expanded in CM, the impact of culture in CM on the expression of a reporter gene driven by the HIV LTR promoter was examined. These experiments reveal that culture in CM represents a potent means of inhibiting the expression of HIV DNA. In this application the term "HIV DNA" refers to genetic material encoding components of HIV which are incorporated into the genome of a host cell, and "expression" refers to transcription or translation by components of the host cell's transcription or translation machinery.

The present invention discloses that the culture of samples containing HIV infected cells in CM not only allows the production of CD4 cell populations expanded to a greater extent than is possible using previously known techniques, but also allows the significant expansion of cell types different from those which could be expanded using previously known techniques, namely CD8 cells and DP cells. Surprisingly, it is possible to expand CD4, CD8 and DP cells together in a single culture using the method of the invention.

T cell populations expanded by the methods of the invention may be further treated to deplete free gp120 from the culture medium, thereby enhancing the survival and activity of the expanded T-cells. Methods employing gp120 binding agents for the selective binding of gp120 are known in the art, and are within the capacity of a skilled technician. For example, anti-gp120 antibodies may be immobilized on a solid support and placed in the culture medium. Free gp120 will tend to bind to the immobilized antibodies and may be removed from the solution by removal of the solid support. In some circumstances the depletion of free gp120 from the culture medium will allow the enhanced survival and reactivity of expanded cell populations. Furthermore, in some instances it will be desirable to deplete the expanded cell populations of HIV infected cells having gp120 on their cell surface using standard methods for the selective binding of gp120. Solid supports may be formed from any biologically acceptable material; however, preferred embodiments include immobilization of gp120 binding agents on the surface of tissue culture plates, and/or on magnetic beads.

Expanded populations containing T cells can be administered to HIV infected subjects to boost their capacity to respond to immunological challenge. Such expanded cell populations may also be modified prior to introduction into the subject to provide a population with desired immunological properties. For example, cells may be exposed to HIV antigens in the presence of MHC compatible antigen presenting cells to induce the activation of cells recognizing the antigen of interest. Potential antigens of interest include, but are not limited to, HIV proteins (such as gp160, gp120, and p24) or peptides or fragments thereof, such as the V3 loop of gp120. In light of the genetic diversity between HIV isolates, it may be desirable to expose cells to a range of HIV antigens from different HIV isolates. Alternatively, it will frequently be possible to induce the activation of HIV-specific cells using an entirely autologous system. For example, a blood sample may be obtained from an HIV infected subject which contains the antigen of interest, suitable antigen-presenting cells, and the cell population to be stimulated. The use of entirely autologous materials reduces the risks and complications associated with using blood components derived from other donors, and it may increase the therapeutic effectiveness of the activated cells by ensuring that the HIV epitopes they recognize are present in the HIV isolate infecting the subject to be treated.

The present invention also provides from another aspect, a means of culturing T cells from HIV infected subjects and assaying the effectiveness of potential antiviral treatments such as culture in CM and/or the use of drug combinations to control viral load. Due to the reduced number of CD4 cells in most subjects infected with HIV, it is not desirable to remove the large numbers of cells needed to generate sufficiently large quantities of cells desirable for drug assay using conventional methods. However, a method allowing the selective culture and expansion of T cells from HIV infected subjects allows such screening. Additionally, the screening method of the present invention allows the monitoring of the response of an HIV infected subject to ongoing drug treatment. For example, it is possible to routinely remove and culture a small sample of LDMNC's from a subject receiving a particular treatment to determine the ongoing effectiveness of that treatment on its own or compared to other alternative treatments. This allows the rapid detection of acquired resistance, thereby facilitating effective disease management on a patient-by-patient basis. Furthermore, the effect of a particular treatment on the subject's immune response may be assessed by examining the variety, specificity, and anti-HIV activity of cells in the sample. Moreover, unlike previous methods, the present method allows the rapid and efficient expansion of numerous cells types, including CD4, CD8, and DP cells. Thus, unlike previous methods, the present method allows the generation of a population for screening which closely resembles the actual cell population existing in the subject in need of treatment. This is extremely valuable, as it is behaved that the levels and activity of both CD4 cells CD8 cells are important in disease prognosis and HIV progression.

The screening method of the present invention may preferably be conducted by the removal of a small blood sample from a patient followed by enrichment of LDMNC's by standard methods as described in Example 2. The LDMNC's are cultured in substantially the same manner as that described in Example 2, except that where only short-term culture is anticipated and large numbers of cells are not required, the LDMNC's may be plated out into 48 or 96-well tissue culture plates to facilitate the study of a larger number of drug combinations. Alternatively, the LDMNC's may be cultured for one or two passages (approximately 4 to 14 days) without the addition of antiviral materials other than CM, following which time the cells may be harvested, diluted to an appropriate level as described in Example 2, and plated out in 24 well plates.

Appropriate levels of various treatments of interest may be commenced immediately after plating out the cells, or the cells may be allowed to remain untreated for 1 to 2 days following plating prior to the commencement of treatment (other than 5% CM which is preferably present in the medium at the time the cells are plated out). The cell count and HIV levels may be determined by standard methods at various times after plating out. The relative abundance and activity of different T cell types may also be determined at various times by methods known in the art. In cases where it is desirable to screen the impact of particular treatments on one of CD4 or CD8 cells, the desired cell type may be isolated from the LDMNC's prior to plating out using conventional methods.

Additionally, cells may be subjected to gene therapy ex vivo to allow the expression of gene products of interest. Such modified cells may be introduced into a subject as a means of therapy or diagnosis. Methods of gene therapy are known in the art. Briefly, expressible genetic material encoding a product of interest is introduced into cells. The treated cells are then screened for the presence of the stably integrated and expressible gene of interest. Cells having the desired characteristics are introduced into an appropriate region of the patient by appropriate means. For example, in some circumstances it may be appropriate to administer cells by intravenous infusion.

Products of interest may include proteins, peptides, and fragments thereof which, when expressed intracellularly, are capable of inhibiting HIV replication. Examples of such compounds are chemokines such as RANTES, MIP-1α, MIP-1β, proteases capable of cleaving viral proteins and rendering them ineffective, protease inhibitors which inhibit the normal post-translational processing of HIV polyproteins, and peptide antagonists of Tat. In some circumstances, products of interest will include antisense RNA complementary to a region of viral RNA and capable of interfering with the formation of virus particles, RNA complementary to an HIV gene expression regulatory element region and capable of interfering with the interaction between this region and its corresponding transcription mediating protein sequence, and ribozymes capable of inhibiting viral replication.

It will also be desirable in some instances to introduce exogenous proteins into expanded cells prior to infusion. Methods for doing this are known in the art. For example, one commercial system, known as "VP22" allows the introduction of fusion proteins into cells. The fusion proteins localize to the nucleus of the cell, where, depending on the protein introduced, they can function to modulate processes occurring in the nucleus, such as aspects of gene expression.

Expanded cell populations may be used immediately, or may be cryopreserved for later use. The method of the present invention is broadly applicable to the expansion of CD4, CD8, and DP cells. An early step in this method comprises the selection of a desired source of target cells. In the practice of the method described herein, one or more types of T cell present in an original cell population can be preferentially expanded to enrich the fraction of the selected lymphocyte in the expanded cell population. Furthermore, desired T cell types may be expanded from an initial cell sample comprising the precursors of the desired cell type. Thus, T cell types present at very low levels in a cell sample can be selectively proliferated to increase their representation in the expanded population. During this expansion of the desired T cells, non-T cells can be allowed to die off, to remain unexpanded, or to fall in number and/or proportion in the expanded culture. One important clinical advantage of the method of this invention is that cell populations containing a fraction of the selected T cells can be produced simply and, in many cases, without the need for separation or purification steps. The method allows for the selective, sequential production of CD4 and CD8 T cells from a single unenriched blood or tissue sample. The present invention further provides a means of expanding a population of DP cells to generate subsets of CD4 cells and CD8 cells. Methods for the generation of CD4 cells and CD8 cells from DP cells are known in the art and it is within the capacity of a competent technician to generate such cells from DP cells as part of the process of the present invention.

An initial population for expansion in CM can be selected from any primary human lymphocyte source. Examples of potential sources include perpheral blood, umbilical cord blood, bone marrow, lymph nodes, thymus, spleen, Peyer's patches or other lymphocyte-containing tissue. Target cells may also be selectively expanded from sources enriched in leukocytes such as material obtained by leukapheresis. Lymphocytes may be derived from healthy subjects or from patients such as those infected with HIV.

Expanded cell populations obtained at each passage may be used directly in immunotherapy of the patient, may be modified further by subculture or genetic manipulation, or may be cryopreserved using standard techniques for use at a later time. Cell banks may be established from patients early after diagnosis of HIV infection as a means of providing autologous T cells for use in the later stages of disease where the immunodeficiency is more pronounced and certain cell types have been irrevocably lost from the patient's blood cell population.

T cells cultured in CM may be further modified by the addition of exogenous recombinant growth factors which promote the proliferation of a T cell population having a desired phenotype or function. Other agents may be added, including growth factors, selective chemicalor biological inhibitors of cell growth, and other antiviral agents that interfere with or suppress HIV replication such as chemokines. Antiviral drugs may also be included in the culture medium as a further step to inhibit viral replication. In light of the present invention it is within the skill of a competent technician to determine what additional antiviral drugs are appropriate. Examples of potentially usefull drugs include reverse transcriptase inhibitors and protease inhibitors such as Zidovidine, Lamivudine, Indinavir, Zerit, Saquinavir, Nelfinavir, and Ritonavir. In some instances Fluconazole will also be useful. Furthermore, the target cell population may be cultured in CM in the presence HIV antigens of interest and appropriate antigen presenting cells and/or target cells to promote the expansion of HIV-specific CD4 and CD8 cells. Such HIV-specific cells may subsequently be infused into an MHC compatible subject who is infected with a strain of HIV expressing epitope recognized by the HIV-specific cells in order to delay HIV progression in that subject.

The Expanded Cell Population

Cultures of T cells expanded in CM typically experience a 4–5 log expansion in 3–4 weeks of culture. CD4 cells, CD8 cells, and DP cells may be obtained, depending on the culture conditions and culture time employed. At each passage the relative abundance of different T-cell types may be assessed using standard techniques. For example, in typical cultures of low density mononuclear cells ("LDMNC's"), CD4 cells predominate during the first two weeks of culture and CD8 cells predominate thereafter. Thus, cultures expanded in CM for two weeks may be used to provide a population that is enriched in CD4 cells. Conversely, cultures expanded for 3–4 weeks may be used to provide a population enriched in CD 8 cells. All cultures may be serum and plasma-free medium, or may be supplemented with autologous or pooled human serum or plasma. Plasma-containing cultures typically convert more quickly and completely from a CD4 dominated population to a CD8 dominated population. Accordingly, plasma may be used to provide both a greater overall T cell expansion, and to provide purer populations of the desired cells.

T cell populations which have been enriched for CD4 cells, CD8 cells, or DP cells may also be expanded in CM. Relatively pure populations of CD4 cells and CD8 cells can be maintained in culture and used to treat subjects as required. Such enriched T cells. expand 3–9 logs in 6–7 weeks, permitting the production of large numbers of therapeutically effective CD4 and CD8 T cells from a small blood sample. Such large cell population expansion also permits the creation of cell banks suitable for use in delayed and repetitive infusions. Populations enriched in CD4 cells and CD8 cells may be recombined prior to infusion where desirable to obtain enhanced therapeutic efficacy.

Uses of the Expanded T Cell Populations

Expanded T cell populations may be used to treat HIV-infected subjects. A subject's own cells may be used to reconstitute his or her immune system throughout disease progression by autolymphocyte therapy. Repetitive or cyclical infusions of autologous T cells derived from cells extracted prior to the or set of significant immunodeficiency can serve as an effective means of fortifying immunity during the later stages of HIV infection when certain T cell populations in the subject's body have been irrevocably lost. The unique ability of CM to expand human umbilical cord blood T cells also permits such cells to serve as a source of lymphocytes for the treatment of HIV infected subjects, provided that the cells are appropriately matched for histocompatibility. For example, HIV infected babies may be treated with T-cells derived from their own umbilical cord blood. Naive T cell populations derived from cord blood may be established for the treatment of HIV infected subjects. Thus, culture in CM permits the use of universal donor lymphocyte banks for immune reconstitution in HIV infection and AIDS.

T cells cultured according to the method of the present invention may be used in a method of screening potential antiviral treatments. Differences between HIV isolates from different subjects can result in inter-patient variability in the effectiveness of many anti-viral strategies, including culture in CM as a means of inhibiting viral replication (excellent expansion of T-cell populations in CM is consistently observed).

It is frequently difficult for physicians to predict in advance what antiviral strategies will be effective in combating the HIV isolate infecting a particular patient. The present invention provides a means for the in vitro culture of cells from a HIV infected patient and an assessment of the effectiveness of the ex vivo culture in CM, as well as both in vivo and ex vivo treatment with various drug combinations on virus levels. In particular, T cells may be obtained from an HIV infected patient and cultured in multiwell plates in a culture medium comprising CM. The levels of supernatant $p24^{gag}$ ("p24") and viral RNA levels may be assessed by standard means. Those patients whose CM-cultured cells have peak p24 supernatant levels of less than 1 ng/ml are suitable patients for large-scale T-cell expansion in CM with or without the use of additional anti-viral agents. Additionally, different drugs or drug combinations of interest may be added to different wells and the impact on virus levels in the sample may be assessed by standard means. Those drug combinations providing adequate viral suppression are therapeutically useful combinations. In light of the invention it is within the capacity of a competent technician to determine what constitutes adequate viral suppression in relation to a particular subject. In order to test the effectiveness of drugs of interest in limiting viral expansion, additional factors such as anti-CD3 antibodies may be added to the culture to stimulate viral production. Unlike culture methods for HIV infected cell samples known in the art, CM allows the culture of T cells for periods of over two months, thereby providing an effective system in which to assay long term drug effectiveness.

T cells produced by the expansion of cells obtained from HIV infected subjects may also be used to treat certain opportunistic infections and tumors directly. Diseases of interest include pneumocycstus carnii, CMV, Kaposi's sarcoma and nonoodgkin's lymphoma. Subject-derived antigen-specific cytolytic T cells can be generated by co-culturing a population of subject-derived T-cells with MHC compatible antigen presenting cells and/or target cells in the presence of the antigen of interest. Antigen presenting cells, target cells, antigen-presenting cells, effector cells, and antigen may be endogenous and patient-specific.

Bone marrow transplants may be used to treat HIV infection itself and/or malignancies resulting from HIV infection. Infusions of autologous lymphocytes, expanded in CM, may be used to support bone marrow transplantation and to reduce the toxicity and risk of infection associated with the procedure.

The method of the invention allows the inhibition of gene expression driven by the HIV LTR promoter region in a cell population by the culture of cells in a medium comprising the CM according to the method of the invention. While it is not intended that the invention should be limited to any theory, it is suspected that culture in CM4 inhibits HIV LTR driven gene expression by altering one or more interactions between transcription mediating proteins and HIV gene expression regulatory elements. Transcription-mediating proteins of interest include host cell encoded proteins such as AP-1, NFkappaB, NF-AT, IRF, LEF-1 and Sp1, and the HIV encoded protein Tat. HIV gene expression regulatory elements of interest include binding sites for AP-1, NFkappaB, NF-AT, IRF, LEF-1 and Sp1, as well as the transacting responsive element ("TAR") which interacts with Tat.

The range of viral levels observed from experiments involving the culture of HIV infected cells obtained from different patients likely reflects, in part, different mutations in the genes encoding transcription mediating proteins and/or HIV gene expression regulatory elements, which compensate for the inhibitory effect of culture in CM according to the method of the invention. Thus, in a preferred embodiment, the HIV infected cells are obtained from a subject with susceptible transcription mediating protein sequences and susceptible HIV regulatory element sequences. In a more preferred embodiment, the HIV infected cells are obtained from a subject having wild-type transcription-mediating protein sequences and wild-type HIV regulatory sequences.

The relationship between Tat and TAR sequence and HIV gene expression has been extensively examined. For example, Garcia et al. (*Genes Dev* 5:2128 (1991)) disclosed that stem structure of TAR RNA stem loop, the primary sequence of the loop, and the bulge element are major determinants for Tat activation. As a further example, Kamine et al. (*Virology* 182:570 (1991)) disclosed regions of the Tat protein sequence important for binding to TAR and found that the basic region of Tat combined with 8 random amino acids allows specific binding of this peptide to TAR. The requirements for tansactivation of HIV transcription by Tat were examined by Kuppuswamy et al. (*Nucleic Acids Research* 17:3551–61, (1989)). Kuppuswamy et al. identified four domains in the N-terminal region of Tat important to transactivation. These and other articles in the prior art allow the assessment of the regions of Tat and TAR necessary for productive interaction. Methods of sequencing RNA and proteins are known in the art and it is within the skill of a competent technician to determine the TAR and Tat sequences in an HIV isolate. In addition to referring to the amino acid and RNA sequences of Tat and TAR, respectively, it is also possible to use methods of molecular modeling known in the art to predict if mutations in these sequences will significantly effect the interaction between Tat and TAR due either to conformational or steric changes or to changes in the phosphorylation pattern of the regions of interest. It is therefore well within the capacity of a technician skilled in the art to identify wild-type sequences and determine if a particular sequence is equivalent to a wild-type sequences.

Similarly, the sequences of transcription mediating proteins such as AP-1, NFkappaB, NIF-AT, IRF, LEF-1 and Sp1, as well as their binding sites, are known in the art. The interactions necessary for productive binding of these transcription mediating proteins and their binding sites have been reported in the prior art and it is within the capacity of a competent technician to determine if a particular mutation will significantly affect the interaction between the transcription mediating protein and its corresponding HIV gene expression regulatory element using the techniques previously discussed with respect to the Tat and TAR sequences.

The phrase "equivalent to wild-type sequence" as used in this application refers to a sequence which differs from wild type sequences only in respect of one or more features which do not significantly affect the interaction between a transcription mediating protein and its HIV gene expression regulatory element. The phrases "susceptible transcription mediating protein sequence" and "susceptible HIV regulatory element sequence" when used in this application, refer to wild type sequences and equivalent to wild-type sequences.

It is well known in the art that there are many strains of HIV and that different strains exhibit different characteristics and responses to treatment. It is to be expected, therefore, that some variability will be observed in the response of cell samples from different patients to culture in CM. However, unlike conventional approaches to HIV treatment which allow an assessment of effectiveness only after extensive treatment (during which time the HIV infection may progress substantially), culture in CM allows a means to determine the effectiveness of the proposed treatment quickly and efficiently.

Although it is known that culture in CM reduces HIV LTR driven gene expression, thereby reducing overall HIV replication, it is believed that several other aspects of CM contribute to its effectiveness. It is known that CM contains RANTES, MIP-1α, and MIP-1β which have been shown to inhibit the initial infection of cells by HIV. Additionally, unlike conventional methods for expanding HIV-infected cell populations, the present invention allows the expansion of significant numbers of CD8 cells and DP cells in the same culture as CD4 cells. CM supports the formation of cytotoxic T-lymphocytes from CD8 cells. Disease prognosis in HIV infection has been correlated to the level of active CD8 cells in the subject's blood. Finally, it is believed that there exist CD8-derived factors which play a role in inhibiting HIV replication (Kinter et al., *PNAS USA* 93(24):14076 (1996)). Thus, CM provides a unique culture system which allows the production of CD8-derived anti-viral factors in a culture containing significant numbers of CD4 cells.

Thus, culture of LDMNC populations in CM is believed to reduce HIV expansion by several means, including: (a) reducing HIV gene expression through an indirect mechanism, (b) inhibiting the infection of cells by HIV indirectly, and (c) allowing the production of a CD8-derived antiviral factor.

The invention is exemplified and demonstrated in the following specific experimental examples.

EXAMPLE 1

Conditioned Medium (CM)

XLCM™—Preferred Embodiment of CM

Human umbilical cord blood containing 20 units of heparin per ml was used as the starting material for the preparation of XLCM (a preferred embodiment of CM), as described in Skea, *Blood* 90:3 680 (1997), Skea, *J. Hematotherapy* 8:129 (1999) and International Publication No. WO 99/33891. Briefly, blood cells were diluted and mezerein was added at a final concentration of 10 ng/ml and the mixture was incubated for 2 hours in a humidified incubator kept at 37° C. and 5% $CO_2$. Concanavalin A was then added at a final concentration of 20 µg/ml and the incubation was continued under the same conditions for four days. The supernatant XLCM was harvested by centrifugation at 500×g for 30 minutes at 4° C., and filtered using a 0.22 µm syringe-mounted filter unit. For the stimulation of cells, XLCM was added to the culture medium at a concentration of 5% by volume. In addition to whole cord blood, whole or buffy coat peripheral or leukapheresis blood from healthy donors or patients may be used to prepare XLCM, as required.

Composition of XLCM

XLCM contains a unique balance of positive and negative regulators of T cell growth. At least 20 known growth regulating factors are present in significant quantities, including chemokines, interleukins, colony stimulating factors and cytokines. Factors of particular interest include: RANTES, MIP-1α, MIP-1β, IFN-γ, and IL-2. It is also noteworthy that XLCM contains only very low levels of IL-6 and IL-4. The relative amounts of several growth regulating factors in XLCM are shown in Table 1, grouped according to concentration as measured by enzyme-linked immunosorbent assay (ELISA). No combination of the recombinant forms of these regulatory factors has been found which reconstitutes the growth promoting activities of XCM.

EXAMPLE 2
Expansion of T Cells from the Low Density Mononuclear Cells of HIV Infected Donors Low density mononuclear cells were prepared from the peripheral blood of HIV infected donors at various stages of disease by density fractionation. These patients had been on a range of drug therapies prior to the donation of these blood samples. Samples of 10–30 ml of whole blood were layered onto an equal volume of a Ficoll-Hypa discontinuous gradient (density 1.077 g/ml) in 50 ml conical tissue culture tubes and centrifuged at 400×g for 30 minutes at room temperature. The interphase material containing LDMNC was collected, and the cells were washed twice in serum-free medium (AIM-V (Sigma) containing 20 units/ml heparin and 50 $\mu$M 2-mercaptoethanol, hereinafter "HBCM-2") by centrifugation at 200×g for 10 minutes at room temperature. The LDMNC were resuspended in HBCM-2, a sample was diluted 1:20 with 2% acetic acid, and the cell count was determined by hemocytometer. The yield of LDMNC per ml of uninfected adult peripheral blood is typically between $1\times10^6$ and $10\times10^6$ (average $1.2\times10^6$). The yield of LDMNC per ml of blood from HIV infected subjects varies, but has been found to be between $0.2\times10^6$ and $3\times10^6$ (average $15\times10^6$). The initial CD4 cell counts from the HIV infected donors examined ranged from 70 to 740 CD4 cells per $\mu$l blood plasma before LDMNC isolation.

The LDMNC were diluted to a final density of $1\times10^5$ cells/ml in HBCM-2 containing 5% XLCM prepared according to the method of Example 1. LDMNC were cultured in the presence or absence of 5% human umbilical cord blood plasma ("P") in 24-well tissue culture plates (1.5 ml/well) and maintained at 37° C. and 5% $CO_2$ in a humidified incubator. No antiviral drugs were present in the in vitro cultures. Every 4 to 7 days the cell count and viability were determined by mixing a sample of the culture suspension with a equal volume of 0.4% trypan blue and counting the unstained (viable) and blue (non-viable) cells by hemocytometer. At each time point, the cells were subcultured by diluting an appropriate volume of the culture to a density of $1\times10^5$ cells/ml in fresh HBCM-2 containing 5% XLCM, with or without 5% P, as appropriate. The fold of expansion of the starting cell number was determined at each passage, and the theoretical total yield calculated assuming the entire culture had been expanded. The cell number at each passage and the maximum fold of expansion of LDMNC from 7 different HIV infected donors are shown in Table 2. The initial CD4 cell count per $\mu$l of blood plasma before LDMNC isolation and time in culture are also shown.

Initial CD4 cell counts ranged from 140 cells per $\mu$l to 740 cells per $\mu$l. XLCM stimulated 1–4 logs of total cell expansion over a culture period from 25 to 44 days. Although the cells expanded well in 5% XLCM alone, the presence of cord plasma significantly improved the level of cell expansion. Indeed, cells from 5 of the 7 HIV infected donors achieved greater than a 5 log expansion in the presence of cord blood plasma. Control LDMNC from three patients stimulated with 5 $\mu$g/ml phytohemagglutinin (PHA) plus 10 U/ml recombinant human interleukin 2 (IL-2), but not XLCM, failed to expand to the first passage.

At selected time points, cultured cells were stained with fluorescently-labeled antibodies to the CD4 and CD8 T cell co-receptors, and were analyzed for the respective antigen expression by flow cytometry. The percent of CD4 cells, CD8 cells, and DP cells in the cell populations derived from 5 of the 7 donors of Table 2 between days 12–28 of culture are shown in Table 3. Surprisingly, in addition to CD4 cells, it was possible to expand therapeutically useful levels of CD8 and DP cells.

EXAMPLE 3
Expansion of Enriched CD4 and CD8 Cells from HIV Infected Donors

CD4 cells were selected from LDMNC prior to culture using anti-CD4 antibody-coated magnetic beads (MiniMacs, Miltenyi Biotec). Positively selected CD4 cells ("CD4-enriched") were eluted from the beads and seeded at $1\times10^5$ cells per ml in HBCM-2 in 24 well tissue culture plates, and cultured in 5% XLCM with or without 5% P, or 5 $\mu$g/ml PHA plus 10 U/ml IL-2 with or without 5% P. The CD4depleted ("CD8 enriched") fraction was similarly cultured. The cells were passaged every 4 to 7 days, depending on their density. Nine passages represents approximately 6 weeks. At each passage culture supernatants and cell pellets were collected and stored at −70° C. for the measurement of virus as described in Example 4.

Overall, the expansion of the enriched CD4 cells in the presence of plasma resulted in a 5 to 32-fold greater expansion than was observed with XLCM alone. Enriched CD8 cells expanded only in XLCM plus plasma.

FIG. 1 depicts the results of expansion of enriched CD4 cells and CD8 cells obtained from three HIV infected subjects and cultured in CM/P or PHA plus IL-2. These cultures represent donors having a range of CD4 cell counts and viral loads. One donor had a relatively high CD4 cell count (530 cells/$\mu$l) and undetectable viral load (<500 copies per ml). The second donor had both a very low CD4 cell count (<150 cells/$\mu$l) and a low viral load (<400 copies/ml), while the third donor had both a very low CD4 cell count (80 cells/$\mu$l) and a very high viral load (534,000 copies/ml). Cells from these patient plus cells from several additional HIV infected donors were similarly cultured and analyzed and the results are depicted in FIGS. 2, 3 and 4. In all cases, XLCM stimulated a strong proliferation of both CD4 and CD8 enriched T cells. The level of T cell expansion in CM/P was significantly greater than that achieved in PHA/IL-2 or PHA/IL-2/P. T cells from donors with low CD4 cell counts and higher viral loads were difficult to culture for even one passage in PHA/IL-2. For cells derived from HIV infected subjects with a CD4 cell count close to normal (>400 cells/$\mu$l), the maximum CD4 T cell expansion was 4 orders of magnitude greater than the total expansion of the same cells stimulated by PHA plus IL-2. T cells from three healthy donors gave similar results, with CD4 cell expansions in CM/P also being four orders of magnitude greater than in PHA plus IL-2.

A comparison of FIG. 1 with FIGS. 2, 3, and 4 reveals that XLCM surprisingly allows the expansion of late culture cell populations which are lost in PHA/IL-2 cultures with or without 5% plasma. In particular, while both XLCM cultures and PHA/IL-2 cultures show a marked reduction in expansion around passage number four (corresponding to approximately day 16), the XLCM cultures continue to expand at a significant rate beyond this point, whereas the PHA/IL-2 cultures tend to become static or die. This effect of XLCM is apparent in respect of both CD4 cell populations and CD8 cell populations, although CD8 cell populations show stronger late culture growth. Moreover, the kinetics of cell population expansion for both CD4 cells and CD8 cells indicates that this late culture growth is due primarily to a distinct cell population which rises in significance after passage 4 and dominates the culture by passage 7. This indicates the presence of a distinct "late culture population" in the XLCM culture cells which is not present in the PHA/IL-2 cultures. Thus, unlike PHA/IL-2, XLCM allows the continued expansion of subpopulations within both CD4 and CD8-enriched cultures.

The late culture population observed may represent HIV-free cells or HIV-resistant cells. A cell population enriched for this late-culture population may be obtained by monitoring the rate of cell expansion and the absolute cell numbers in an expanding cell population and harvesting the expanded cell population at or after the first passage in which a recovery of cell expansion rate is observed following the sharp decline. For example, for the cell population depicted in FIG. 2, a cell population enriched for the late-culture population could be obtained by harvesting the cell population at or after passage 5. A cell population comprising a substantially pure population of the late culture population may be obtained by harvesting the expanded cell population several passages after the cell population becomes enriched for the late culture population after the point where the total number of cells in the culture is at least 2 and preferably at least three orders of magnitude higher than it was at the time the culture became enriched for the late culture population. For example, for the cell population depicted in FIG. 2, a substantially pure late culture population could be obtained by harvesting the cell population after passage 7.

The median fold expansion for CD4-enriched and CD8-enriched cell populations from 21 HIV infected subjects, broken down by CD4 cell count, are depicted in Table 4. HIV infected subjects were classified into three disease stages based on their peripheral blood CD4 cell count: (1) CD4 count above 400/mm$^3$—still relatively healthy, (2) CD4 count between 200 and 400 cells/m$^3$—progressing towards AIDS, and (3) CD4 count below 200/mm$^3$—AIDS. CD4 cells and CD8 cells were isolated and expanded with CM/P. These data represent the results of 44 experiments using 27 blood samples obtained from a total of 21 different patients. Very large cell expansions were achieved even when the starting CD4 cell counts were very low.

EXAMPLE 4
Suppression of HIV Replication by CM

Table 5 summarizes the CD4 and CD8 cell counts, viral load and peak soluble p24$^{gag}$ observed in expanded populations of CD4-enriched cells obtained from 16 patients. Viral load was determined by reverse-transcriptase polymerase chain reaction (RT-PCR) amplification of the HIV-1 RNA gag sequence from donor plasma, and is expressed as RNA copies per ml. The RT-PCR limit of detection was 400–500 copies/ml and for the purposes of this study measurements below this value are considered undetectable. CD4 cells were isolated and expanded with CM/P. At each passage, culture supernatants were collected and soluble HIV p24$^{gag}$ w was measured by ELISA (Oigamon-Tecknika). The ELISA limit of detection was 0.005 ng p24/ml. The peak p24$^{gag}$ level measured over the course of each culture is reported. In 12 cultures, the concentration of p24$^{gag}$ was less than 1 ng/ml indicating very low levels of viral replication. In 6 cultures p24$^{gag}$ was undetectable. In only 2 cases were very high levels of p$_{24}^{gag}$ observed, and these did not correlate with low CD4 counts or high viral loads.

Thus, XLCM can stimulate vigorous CD4 cell, CD8 cell and DP cell proliferation from HIV infected donors without high levels of virus replication. XLCM therefore offers a significant addition to current drug therapies for the treatment of HIV-infected individuals over a wide range of donors and disease states by permitting the in vitro expansion and reinfusion of their own CD4 cells, CD8 cells, and DP cells as a means of reconstituting or maintaining their immune system.

EXAMPLE
Suppression of HIV LTR-driven Gene Expression by CM

The effect of XLCM on LTR-driven gene expression was studied on a human CD4 T cell line. $3 \times 10^7$ Jurkat cells were tansfected by the DEAE-dextran DNA transfection method with 10 µg of a DNA construct containing the chloramphenicol acetyltransferase (CAT) gene under the control of the HIV LTR promoter together with 5 µg of a plasmid carrying the HIV tat regulatory sequence. Immediately after transfection the cells were placed in 25% CM/10% FBS/RPMI. Twenty-four hours later, cells were stimulated with 25 ng/ml phorbol myristate acetate (PMA) and 2 µM ionomycin for 18 hours, lysed, and the level of CAT expression was determined by ELISA.

HIV LTR-transfected Jurkat cells cultured in XLCM produced 950 pg CAT compared to 2,530 pg CAT in the absence of CM, representing a 62% reduction. These data demonstrate that XLCM substanially'suppresses LTR gene expression in a T cell line and indicate that XLCM also suppresses viral replication in primary cultures of T cells by suppressing HIV LTR-driven gene expression.

While the invention will be described in conjunction with illustrated embodiments, it will be understood that it is not intended to limit the invention to such embodiments. On the contrary, it is intended to cover all alternatives, modifications and equivalents as may be included within the spirit and scope of the invention as defined by the appended claims.

TABLE 1

Cytokines in CM

| Cytokine | Concentration* in CM (ng/ml) | Range (ng/ml) |
| --- | --- | --- |
| IL-8 | 234 | 181–>1000 |
| TNF-β | 112 | 98–160 |
| MIP-1α | 98 | 68–243 |
| IL-2 | 44 | 12–159 |
| TGF-β1 | 21 | 6.9–44 |
| RANTES | 15 | 4–54 |
| MIP-1β | 11 | 1–39 |
| GM-CSF | 11 | 0.7–24 |
| TNF-RII | 9.1 | 6.8–17 |
| IL-1β | 6.4 | 0.2–18 |
| M-CSF | 5.4 | 2.3–9.7 |
| IL-13 | 3.6 | 1.5–13 |
| IFN-γ | 3.6 | 0.6–14 |
| IL-1α | 2.3 | 0.004–4.9 |
| IL-16 | 2.1 | 0.5–6 |
| TNF-RI | 1.8 | 1.1–2.4 |
| Fas | 1.3 | <0.04–2.3 |
| TNF-α | 0.37 | <0.001–3.4 |
| IL-12 | 0.26 | 0.07–0.8 |
| SCF | 0.2 | 0.15–0.29 |
| IL-10 | 0.02 | 0.007–0.2 |
| IL-6 | 0.007 | <0.006–0.028 |
| IL-4 | 0.0068 | 0.00012–0.08 |

*median concentration of cytokine measured in n = 6–18 independent lots of CM using commercial ELISA kits: IL-1β, IL-2, IL-4, IL-6, IL-8, IL-10, IL-12, IL-13, RANTES, TGF-β1, TNF-RI, TNF-RII, Fas, (Biosource International, Camarillo, CA), INF-γ (Genzyme Diagnostics, Cambridge, MA), IL-16 (Immuno Diagnostics Inc., Buffalo, NY), TNF-α, GM-CSF, MIP-1α (Intergen Company, Purchase, NY) and MIP-1β, TNF-β, IL-1α, SCF, M-CSF (R & D Systems, Minneapolis, MN).

TABLE 2

Expansion of LDMNC from HIV+ Donors in XLCM ™

| Donor | CD4 Count/ul | Condition | Viable Cells (× 10⁻³)/ml Passage Number | | | | | | Maximum Fold Expansion | Culture Time, days |
|---|---|---|---|---|---|---|---|---|---|---|
| | | | 1 | 2 | 3 | 4 | 5 | 6 | | |
| 91-00119 | 140 | XLCM ™/P | 8.6 | 5.6 | 21.4 | 1.8 | — | — | 1,855 | 25 |
| | | XLCM ™ | 1.0 | 3.0 | 1.8 | — | 2.2 | | 12 | 32 |
| 96-00570 | 160 | XLCM ™/P | 17.8 | 25.0 | 17.6 | 8.0 | 3.2 | 4.0 | 801,997 | 41 |
| | | XLCM ™ | 2.2 | 19.0 | 8.8 | 3.6 | 2.4 | — | 3,178 | 34 |
| 96-00555 | 180 | XLCM ™/P | 1.2 | 23.8 | 21.2 | 7.8 | 4.8 | 3.4 | 73,122 | 39 |
| | | XLCM ™ | 1.0 | 13.2 | 6.8 | 5.6 | 2.6 | 2.2 | 2,875 | 39 |
| 92-00233 | 400 | XLCM ™/P | 9.2 | 19.8 | 22.4 | 9.4 | 7.2 | 3.2 | 883,713 | 41 |
| | | XLCM ™ | 8.4 | 18.0 | 14.0 | 6.2 | 4.2 | — | 55,121 | 34 |
| 92-00265 | 430 | XLCM ™/P | 12.6 | 21.6 | 35.8 | 14.4 | 6.4 | — | 897,945 | 32 |
| | | XLCM ™ | — | 9.8 | 16.6 | 6.2 | 5.6 | — | 5,648 | 32 |
| 94-00391 | 440 | XLCM ™/P | 13.8 | 25.4 | 23.8 | 10.2 | 2.5 | 1.7 | 361,642 | 41 |
| | | XLCM ™ | 9.4 | 18.8 | 23.8 | 4.4 | 3.1 | 1.1 | 63,106 | 44 |
| 93-00378 | 740 | XLCM ™/P | 19.2 | 52.8 | 40.8 | 48.8 | — | — | 2,018,437 | 28 |
| | | XLCM ™ | 8.6 | 13.6 | 21.6 | 30.4 | — | — | 76,801 | 28 |

TABLE 3

Percent CD4+ and CD8+ T Cells in LDMNC from HIV+ Donors

| Donor | Condition | Time, days | % CD4+ | % CD8+ | % CD4+/CD8+ Double Positives |
|---|---|---|---|---|---|
| 91-00119 | XLCM ™/P | 12 | 22 | 83 | 8 |
| | | 25 | 8 | 87 | 3 |
| | XLCM ™ | 12 | 42 | 46 | 7 |
| | | — | — | — | — |
| 96-00555 | XLCM ™/P | 12 | 43 | 69 | 15 |
| | | 25 | 23 | 83 | 9 |
| | XLCM ™ | 12 | 52 | 43 | 6 |
| | | 25 | 60 | 25 | 3 |
| 92-00265 | XLCM ™/P | 12 | 67 | 42 | 11 |
| | | 25 | 33 | 73 | 10 |
| | XLCM ™ | 12 | 69 | 16 | 3 |
| | | 25 | 67 | 14 | 3 |
| 96-00570 | XLCM ™/P | 17 | 34 | 79 | 14 |
| | XLCM ™ | 17 | 59 | 50 | 15 |
| 93-00378 | XLCM ™/P | 15 | 53 | 38 | 12 |
| | | 28 | 12 | 93 | 15 |
| | XLCM ™ | 15 | 66 | 27 | 4 |
| | | 28 | 69 | 21 | 5 |

TABLE 4

Expansion of T Cells from HIV+ Patients At Different Stages of Disease

| | Stage of Disease | | |
|---|---|---|---|
| | CD4 Count > 400/mm³ | CD4 Count 200–400/mm³ | CD4 Count < 200/mm³ |
| CD4 + T lymphocytes | | | |
| Median Fold of Expansion | $8 \times 10^4$ | $6 \times 10^4$ | $9 \times 10^4$ |
| Range | $2 \times 10^3 – 2 \times 10^8$ | $2 \times 10^2 – 2 \times 10^5$ | $2 \times 10^1 – 2 \times 10^9$ |
| n | 9 | 6 | 11 |
| CD8 + T lymphocytes | | | |
| Median Fold of Expansion | $1 \times 10^6$ | $1 \times 10^5$ | $4 \times 10^6$ |
| Range | $1 \times 10^5 – 7 \times 10^7$ | $1 \times 10^4 – 3 \times 10^5$ | $1 \times 10^4 – 7 \times 10^9$ |
| n | 4 | 5 | 9 |

TABLE 5

Viral Replication During Culture of T Cells from HIV+ Patients with CM

| Patient | CD4 Count (cells/μl) | CD8 Count (cells/μl) | Viral Load (virus/ml plasma) | Peak p24 Level (ng/ml) |
|---|---|---|---|---|
| 558 | 700 | nd | <500 | 0.006 |
| 116 | 540 | nd | <500 | <0.005 |
| 433 | 530 | 850 | <500 | <0.005 |
| 391 | 500 | 660 | <500 | <0.005 |
| 546 | 500 | nd | <500 | 1400 |
| 478 | 480 | nd | 25730 | 0.18 |
| 431 | 470 | 560 | 452 | 0.07 |
| 292 | 440 | nd | <500 | 1.45 |
| 233 | 400 | 1090 | 29010 | <0.005 |
| 632 | 390 | nd | <500 | 11.5 |
| 435 | 190 | 1270 | <500 | <0.005 |
| 268 | 180 | 1100 | <500 | 0.17 |
| 570 | 160 | 670 | <500 | <0.005 |
| 432 | 150 | 580 | <500 | 0.006 |
| 491 | 80 | 700 | 333000 | 900 |
| 634 | 70 | 250 | 683000 | 0.75 | nd = not done

What we claim as our invention:

1. A method of obtaining an expanded population of target T cells with reduced levels of HIV-1 from an initial population of T cells obtained from a subject infected with HIV-1, the method comprising:
   (1) preparing a conditioned medium (CM) by incubating a starting population of umbilical cord blood cells in a growth medium containing at least two plant-derived mitogens wherein the two plant derived mitogens are mezerin and concanavalin A and
   (2) culturing the initial population of T cells in the presence of an effective amount of a culture medium comprising the CM from step (1), to expand the population of target T cells in the culture while maintaining reduced levels of HIV-1.

2. The method of claim 2 wherein the supernatant p24 levels are less than 0.1

3. The method of claim 1 wherein the starting population of blood cells comprises human umbilical cord blood cells.

4. The method of claim 1 wherein the CM is prepared from a starting population of blood cells obtained from a subject not infected with HIV-1.

5. The method of claim 1 wherein the CM is prepared from a starting population of blood cells obtained from the same source as the initial cell population.

6. The method of claim 1 wherein the expanded T cell population comprises a T cell type selected from the group consisting of CD8 cells, CD4 cells, and double positive CD4 and CD8 cells.

7. The method of claim 1 wherein the expanded cell population is further monitored during culturing to determine the relative levels of different T-cell types at each passage.

8. The method of claim 1 wherein the initial cell population is obtained from a subject infected with HIV-1.

9. The method of claim 1 wherein the initial cell population is obtained from a subject infected with an isolate of HIV-1 having wild-type HIV-1 gene expression regulatory element sequences.

10. The method of claim 1 wherein the initial cell population is obtained from a subject infected with an isolate of HIV-1 having wild-type transcription mediating protein sequences.

11. The method of claim 9 wherein the isolate of HIV-1 further has wild-type transcription mediating protein sequences.

12. The method of claim 1 wherein the subject had a pretreatment CD4 count of >50 cells/$\mu$l.

13. The method of claim 1 wherein the subject had a pretreatment CD4 count of >100 cells/$\mu$l.

14. The method of claim 1 wherein the subject had a pretreatment CD4 count of >200 cells/$\mu$l.

15. The method of claim 1 wherein the subject had a pretreatment CD4 count of >400 cells/$\mu$l.

16. The method of claim 1 wherein the subject had a pretreatment CD4 count of >800 cells/$\mu$l.

17. The method of claim 1 wherein the subject had a pretreatment CD8 count of >200 cells/$\mu$l.

18. The method of claim 1 wherein the subject had a pretreatment CD8 count of >400 cell/$\mu$l.

19. The method of claim 1 wherein the subject had a pretreatment CD8 count of >800 cell/$\mu$l.

20. The method of claim 1, wherein the culture medium further includes human plasma.

21. The method of claim 1 wherein the culture medium further includes human serum.

22. The method of claim 1, wherein the culture medium further includes human cord blood plasma.

23. The method of claim 1 wherein the culture medium further includes at least one antiviral compound.

24. The method of claim 1 or 20 wherein the culture is further depleted of free gp120.

25. The method of claim 1 wherein the culture is further depleted of cells having gp120 on their surface.

26. The method of claim 1 wherein the target cells are additionally subjected to gene transfection ex vivo.

27. The method of claim 1 wherein the target cell population is further exposed to one or more inhibitors of HIV replication.

28. The method of claim 27 wherein the inhibitor of HIV replication is an anti-viral drug.

29. The method of claim 1 wherein the target cell population is further exposed to a drug selected from the group comprising: Zidovidine, Lamivudine, Indinavir, Zerit, Saquinavir, Nelfinavir, and Ritonavir.

30. The method of claim 1 wherein the target cells are additionally screened for susceptibility to one or more treatments.

31. The method of claim 30 wherein the treatment is anti-viral drug treatment.

32. The method of claim 30 wherein the treatment is ex vivo gene transfection.

33. A method of obtaining an expanded population of target T cells with supernatant p24 levels of less than 1 ng/ml from an initial population of T cells obtained from a suitable subject infected with HIV-1 comprising:
   (1) preparing a conditioned media (CM) by incubating a starting population of umbilical cord blood cells in a growth medium containing at least two plant-derived mitogens wherein the two plant derived mitogens are mezerin and concanavalin A; and
   (2) culturing an initial population of T cells in the presence of an effective amount of the CM from step (1), to expand the population of target T cells in the culture while maintaining reduced levels of HIV-1.

* * * * *

UNITED STATES PATENT AND TRADEMARK OFFICE
CERTIFICATE OF CORRECTION

PATENT NO. : 6,610,542 B1  Page 1 of 1
DATED : August 26, 2003
INVENTOR(S) : David N. Bell and Kenneth Lee Rosenthal It is certified that error appears in the above-identified patent and that said Letters Patent is hereby corrected as shown below:

<u>Title page,</u>
Item [54], Title, replace "CD8-" with -- CD8+ --.

Signed and Sealed this

Twentieth Day of April, 2004

JON W. DUDAS
*Acting Director of the United States Patent and Trademark Office*